US012605246B2

(12) United States Patent
King et al.

(10) Patent No.: US 12,605,246 B2
(45) Date of Patent: Apr. 21, 2026

(54) PROSTHETIC HEART VALVE WITH ATRIAL DRAIN

(71) Applicant: St. Jude Medical, Cardiology Division, Inc., St. Paul, MN (US)

(72) Inventors: Alec King, Maple Grove, MN (US); Grayston Licht, Riverside, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 481 days.

(21) Appl. No.: 18/461,561

(22) Filed: Sep. 6, 2023

(65) Prior Publication Data

US 2024/0173128 A1 May 30, 2024

Related U.S. Application Data

(60) Provisional application No. 63/384,986, filed on Nov. 25, 2022.

(51) Int. Cl.
A61F 2/24 (2006.01)
A61F 2/00 (2006.01)
A61F 2/06 (2013.01)

(52) U.S. Cl.
CPC .... *A61F 2/2418* (2013.01); *A61F 2002/0081* (2013.01); *A61F 2002/068* (2013.01); *A61F 2220/0041* (2013.01); *A61F 2220/0075* (2013.01); *A61F 2230/0054* (2013.01); *A61F 2250/001* (2013.01); *A61F 2250/0063* (2013.01); *A61F 2250/0069* (2013.01)

(58) Field of Classification Search
CPC ............ A61F 2/2418; A61F 2002/0081; A61F 2002/068; A61F 2220/0041; A61F 2220/0075; A61F 2230/0054; A61F 2250/001; A61F 2250/0063; A61F 2250/0069
See application file for complete search history.

(56) References Cited

U.S. PATENT DOCUMENTS

| | | | | |
|---|---|---|---|---|
| 10,441,416 B2 * | 10/2019 | Oba | ...................... | A61F 2/2418 |
| 10,695,177 B2 * | 6/2020 | Hariton | ................. | A61F 2/2418 |
| 2018/0055629 A1 * | 3/2018 | Oba | ...................... | A61F 2/2409 |
| 2018/0116798 A1 * | 5/2018 | Perszyk | ................. | A61F 2/2445 |
| 2019/0046317 A1 * | 2/2019 | Murad | .................. | A61F 2/2445 |

(Continued)

FOREIGN PATENT DOCUMENTS

| | | | | |
|---|---|---|---|---|
| CN | 107920897 A | * | 4/2018 | .......... A61F 2/2418 |
| CN | 209678758 U | | 11/2019 | |

(Continued)

*Primary Examiner* — Tan-Uyen T Ho
(74) *Attorney, Agent, or Firm* — SLEMAN & LUND LLP

(57) ABSTRACT

A prosthetic heart valve includes an outer frame, an outer sealing skirt, an inner frame, an inner sealing skirt, a plurality of prosthetic leaflets mounted within the inner frame, and a plurality of connecting arms connecting the inner frame to the outer frame so that the inner frame is positioned radially inward of the outer frame. A bridging skirt extends from the outer sealing skirt to an inflow edge of the inner sealing skirt. The bridging skirt covers a gap between the inner frame and the outer frame. The inner sealing skirt may include at least one trench that interrupts an otherwise circular shape of the inflow edge of the inner sealing skirt, the trench extending in an outflow direction of the prosthetic heart valve.

20 Claims, 5 Drawing Sheets

(56)     References Cited

U.S. PATENT DOCUMENTS

2019/0321171  A1*  10/2019  Morriss ................. A61F 2/2436
2022/0313428  A1*  10/2022  Bergin  ................. A61F 2/2418

FOREIGN PATENT DOCUMENTS

CN          212522085  U      2/2021
WO          2016172349  A1    10/2016
WO      WO-2017096157  A1  *   6/2017   ............ A61F 2/246

* cited by examiner

PROSTHETIC HEART VALVE WITH ATRIAL DRAIN

CROSS-REFERENCE TO RELATED APPLICATIONS

This application claims priority to the filing date of U.S. Provisional Patent Application No. 63/384,986, filed Nov. 25, 2022, the disclosure of which is hereby incorporated by reference herein.

BACKGROUND OF THE DISCLOSURE

Heart valve disease is a significant cause of morbidity and mortality. One treatment for this disease is valve replacement. One form of replacement device is a bioprosthetic valve. Collapsing these valves to a smaller size or into a delivery system enables less invasive delivery approaches compared to conventional open-chest, open-heart surgery. Collapsing the implant to a smaller size and using a smaller delivery system minimizes the access site size and reduces the number of potential periprocedural complications.

Native atrioventricular valves (i.e., the tricuspid valve and the mitral valve) typically have a larger size and/or diameter compared to the native aortic valve and the native pulmonary valve. Among the native atrioventricular valves, a regurgitant tricuspid valve typically has a larger size and/or diameter than a regurgitant mitral valve. For example, for patients with severe tricuspid valve regurgitation, the diameter of the tricuspid valve may range from about 40 mm to about 66 mm, although these numbers are merely exemplary. As a result, prosthetic heart valve designs and considerations for replacing the different native heart valves are not identical. For example, to accommodate the large size of the mitral and tricuspid valve, prosthetic atrioventricular heart valves may include an outer frame with a large size to engage the native mitral or tricuspid annulus, and a smaller and generally cylindrical inner frame within that outer frame, the inner frame housing the prosthetic valve leaflets.

BRIEF SUMMARY

According to one aspect of the disclosure, a prosthetic heart valve for replacing a native heart valve includes a collapsible and expandable outer frame configured to be positioned within an annulus of the native heart valve, an outer sealing skirt being positioned on a luminal or abluminal surface of the outer frame. The prosthetic heart valve may include a collapsible and expandable inner frame, an inner sealing skirt positioned on a luminal or abluminal surface of the inner frame, a plurality of prosthetic leaflets coupled to the inner sealing skirt or the inner frame, and positioned within the inner frame, and a plurality of connecting arms connecting the inner frame to the outer frame so that the inner frame is positioned radially inward of the outer frame. A bridging skirt may extend from the outer sealing skirt to an inflow edge of the inner sealing skirt, the bridging skirt covering a gap between the inner frame and the outer frame. The inner sealing skirt may include at least one trench that interrupts an otherwise circular shape of the inflow edge of the inner sealing skirt, the trench extending in an outflow direction of the prosthetic heart valve. Stated differently, the trench may be sloped to empty residual fluid toward an outflow direction of the prosthetic heart valve. The inner frame may include cells arranged circumferentially in an atrial row of cells. The at least one trench may form a "V"-shape that follows struts of two circumferentially adjacent cells in the atrial row of cells. The at least one trench may include a plurality of trenches. The plurality of trenches may include three trenches. The inner frame may include three commissure attachment features extending at an outflow end of the inner frame, adjacent ones of the plurality of prosthetic leaflets being coupled to a corresponding one of the commissure attachment features, each of the three trenches being axially aligned with a corresponding one of the three commissure attachment features. The inflow edge of the inner sealing skirt may traverse a circumferential arc along an inflow end of the inner frame in a circumferential direction of the inner frame between circumferentially adjacent pairs of the plurality of trenches, so that the "V"-shapes of the plurality of trenches are positioned in the outflow direction of the prosthetic heart valve compared to the arc. The bridging skirt may include an outer perimeter attached to the outer sealing skirt, and an inner perimeter attached to the inner sealing skirt. The inner perimeter of the bridging skirt may follow the circumferential arc of the inflow edge of the inner sealing skirt between adjacent pairs of the plurality of trenches, and may follow the "V"-shapes of the plurality of trenches at the trenches. In an expanded condition of the prosthetic heart valve, bottoms of the "V"-shapes of the plurality of trenches may be positioned at outflow-most positions of the bridging fabric. In an implanted condition of the prosthetic heart valve, the bridging skirt in combination with the inner sealing skirt may form flow pathways that preferentially channel blood that flows toward the bridging skirt to drain into the inner frame via the plurality of trenches.

The plurality of connecting arms may have a first end coupled to the inner frame, and a second free end opposite the first end, the second free ends of the plurality of connecting arms being coupled to the outer frame. The second free ends of the plurality of connecting arms may each define an aperture, the second free ends of the plurality of connecting arms being coupled to the outer frame via fasteners passing through the apertures. The fasteners may be sutures or rivets. The first end of each of the plurality of connecting arms may be formed integrally with the inner frame. In an expanded condition of the prosthetic heart valve, the plurality of connecting arms may maintain an inflow end of the inner frame at an axial distance from an inflow end of the outer frame, so that the inflow end of the outer frame is positioned in an outflow direction of the prosthetic heart valve relative to the inflow end of the inner frame. The outer sealing skirt may be a separate structure from the bridging skirt, and the bridging skirt may be a separate structure from the inner sealing skirt. An outer perimeter of the bridging skirt may be sutured to the outer sealing skirt, and an inner perimeter of the bridging skirt may be sutured to the inner sealing skirt. The bridging skirt may be sutured to the plurality of connecting arms. The prosthetic heart valve may be sized and shaped for replacing a native right atrioventricular valve.

DETAILED DESCRIPTION

As used herein, the term "inflow end," when used in connection with a prosthetic heart valve, refers to an end (e.g., atrial end) of the prosthetic heart valve into which blood first flows when the prosthetic heart valve is implanted in an intended position and orientation. On the other hand, the term "outflow end," when used in connection with a prosthetic heart valve, refers to the end (e.g., ventricular end) of the prosthetic heart valve through which blood exits when the prosthetic heart valve is implanted in an intended position and orientation. In the figures, like numbers refer to like or identical parts. As used herein, the terms "substantially," "generally," "approximately," and "about" are intended to mean that slight deviations from absolute are included within the scope of the term so modified. When ranges of values are described herein, those ranges are intended to include sub-ranges. For example, a recited range of 1 to 10 includes 2, 5, 7, and other single values, as well as all sub-ranges within the range, such as 2 to 6, 3 to 9, 4 to 5, and others.

The present disclosure is generally directed to collapsible prosthetic atrioventricular (tricuspid and mitral) valves and in particular features of sealing skirts and stents thereof to minimize or eliminate stagnation of blood that contacts the prosthetic heart valve. And while the benefits of the prosthetic heart valves described herein may be particularly suited to a native tricuspid valve replacement due to the particular anatomical environment of the native tricuspid valve, as well as the relatively lower pressures within the right heart compared to the left heart, the concepts disclosed herein may apply to both prosthetic tricuspid valves and prosthetic mitral valves.

Figure 1:
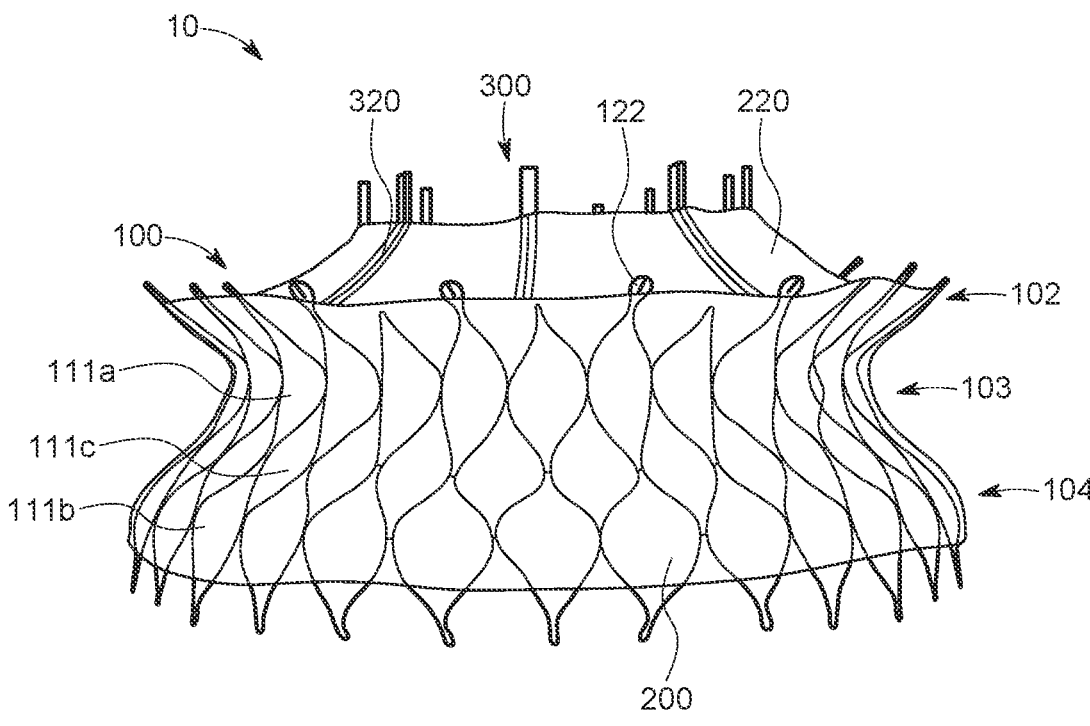
FIG. 1 is a perspective view of a prosthetic heart valve in an expanded configuration according to an aspect of the disclosure.

FIG. 1 is a side view of a prosthetic atrioventricular heart valve 10 according to one aspect of the disclosure. FIG. 1 shows an exemplary outer frame 100 that may be used with the prosthetic heart valve 10, the outer frame 100 being in an expanded or deployed configuration in FIG. 1. The outer frame 100 (which may also be referred to herein as a stent) may be configured to at least partially surround an inner frame 300 (which is mostly not visible in FIG. 1) to which a plurality of prosthetic leaflets 500 (which are not at all visible in FIG. 1) are mounted, described in greater detail below. The outer frame 100 may be primarily for anchoring the prosthetic heart valve within the native heart valve annulus, while the inner frame 300 may be primarily for holding the prosthetic valve assembly (which includes the prosthetic leaflets 500) in the desired position and orientation.

Outer frame 100 may include an atrial portion or anchor 102, a ventricular portion or anchor 104, and a central or waist portion 103 coupling the atrial portion to the ventricular portion. Central or waist portion 103 may be between atrial portion 102 and ventricular portion 104. Atrial portion 102 may be configured and adapted to be disposed on an atrial side of a native valve annulus and may flare radially outwardly from the central portion 103 in the expanded or deployed condition. Ventricular portion 104 may be configured and adapted to be disposed on a ventricle side of the native valve annulus, and may also flare radially outwardly from the central portion 103 when in the expanded or deployed condition. The central portion 103 may be configured to be situated in the valve orifice, for example in contact with the native valve annulus. In use, the atrial portion 102 and ventricle portion 104 may lie on opposite sides of the native valve annulus on the atrial and ventricular sides thereof, respectively, helping to hold the prosthetic heart valve in place.

The atrial portion 102 may be formed as a portion of a stent or other support structure that includes or is formed by a plurality of generally diamond-shaped cells, although other suitable cell shapes, such as triangular, quadrilateral, or polygonal may be appropriate. In some examples, the atrial portion 102 may be formed as a braided mesh, as a portion of a unitary stent, or a combination thereof. According to one example, the stent that includes the atrial portion 102 may be laser cut from a tube of nitinol and shape-set (e.g., via heat treatment) to the desired shape so that the stent, including atrial portion 102, is collapsible for delivery, and re-expandable to the set-shape during deployment. The atrial portion 102 may be heat set into a suitable shape to conform to the native anatomy of the valve annulus to help provide a seal and/or anchoring between the atrial portion 102 and the native valve annulus. The shape-set atrial portion 102 may be partially or entirely covered by a cuff or skirt 200, on the luminal and/or abluminal surface of the atrial portion 102. The skirt 200 may be formed of any suitable material, including biomaterials such as bovine pericardium, biocompatible polymers such as ultra-high molecular weight polyethylene, woven polyethylene terephthalate ("PET"), or expanded polytetrafluoroethylene ("ePTFE"), or combinations thereof. The atrial portion 102 may include features for connecting the atrial portion to a delivery system. For example, the atrial portion 102 may include pins or tabs 122 around which sutures (or suture loops) of the delivery system may wrap so that while the suture loops are wrapped around the pins or tabs 122, the outer frame 100 maintains a connection to the delivery device.

The ventricular portion 104 may also be formed as a portion of a stent or other support structure that includes or is formed of a plurality of diamond-shaped cells, although other suitable cell shapes, such as triangular, quadrilateral, or polygonal may be appropriate. In some examples, the ventricular portion 104 may be formed as a braided mesh, as a portion of a unitary stent, or a combination thereof. According to one example, the stent that includes the ventricular portion 104 may be laser cut from a tube of nitinol and shape-set (e.g., via heat treatment) to the desired shape so that the stent is collapsible for delivery, and re-expandable to the set-shape during deployment. The ventricular portion 104 may be partially or entirely covered by a cuff or skirt 200, on the luminal and/or abluminal surface of the ventricular portion 104. Skirt 200 may be formed of any suitable material described above in connection with the skirt of atrial portion 102. It should be understood that the atrial portion 102, the central portion 103, and the ventricular portion 104 may be formed as portions of a single support structure (including as an integral or monolithic unit), such as a single stent or braided mesh, and the skirt 200 may be formed as a single structure if desired. However, in other embodiments, the atrial portion 102, central portion 103, and/or ventricular portion 104 may be formed separately and coupled with one another, as may the skirt 200.

The outer frame 100 may be configured to expand circumferentially (and radially) and foreshorten axially as the prosthetic heart valve expands from the collapsed delivery configuration to the expanded deployed configuration. As described herein, the outer frame 100 may define a plurality of atrial cells 111a in one circumferential row on the inflow side of outer frame 100, a plurality of ventricular cells 111*b* in another circumferential row on the outflow side of outer frame 100, and a plurality of central cells 111*c* between the atrial cells 111*a* and the ventricular cells 111*b*. Each of the plurality of cells 111*a-c* may be configured to expand circumferentially and foreshorten axially upon expansion of the outer frame 100. As shown, cells 111*a-c* may all be diamond-shaped. With the particular set shape of outer frame 100 shown in FIG. 1, the atrial cells 111*a* may form a general "C"-shape in with the terminal inflow end of the atrial cells 111*a* flaring radially outwardly to hook over the atrial portion of the native valve annulus, a center area of the atrial cells 111*a* may define a minimum diameter of the outer frame, with the terminal outflow end of the atrial cells 111*a* starting to flare back outwardly in the direction of the ventricular portion 104. The central cells 111*c* may have a terminal inflow end that is positioned at or adjacent to the minimum diameter of the outer frame 100, with the central cells 111*c* continuing the outward flare in the direction of the ventricular portion 104. The ventricular cells 111*b* may continue to flare radially outwardly and define the largest diameter of the outer frame 100. In some embodiments, the terminal outflow ends of the ventricular cells 111*b* may begin to hook slightly back toward the central longitudinal axis of the outer frame 100 so as to present an atraumatic termina outflow end. Although cells 111*a*-111*c* are shown as being diamond-shaped, other shapes of cells (and other numbers of cells or numbers of rows of cells) than are shown may be suitable.

Figure 2:
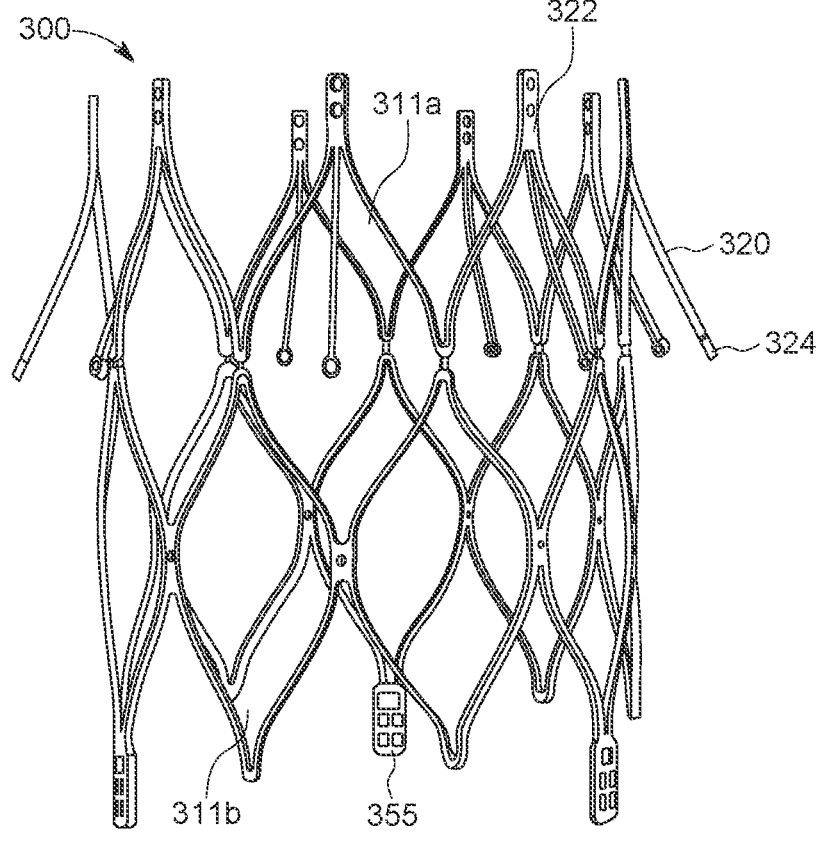
FIG. 2 is a perspective view of an exemplary inner frame that may be used with the prosthetic heart valve of FIG. 1.
Figure 3:
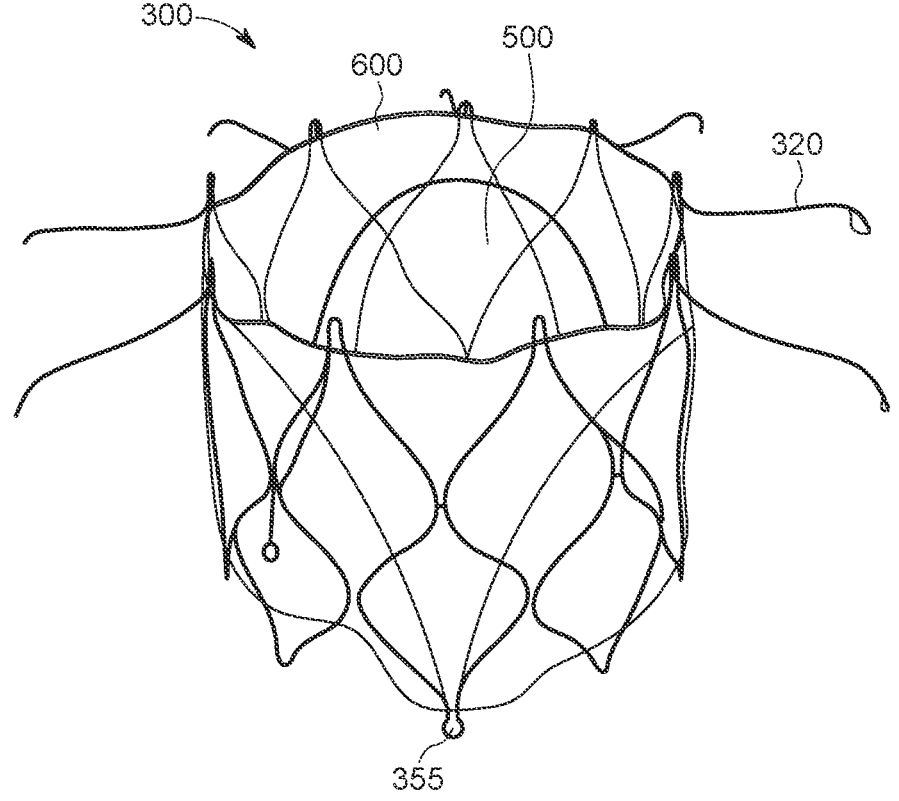
FIG. 3 is a perspective view of the inner frame of FIG. 2 with a valve assembly mounted to the inner frame.
Figure 4:
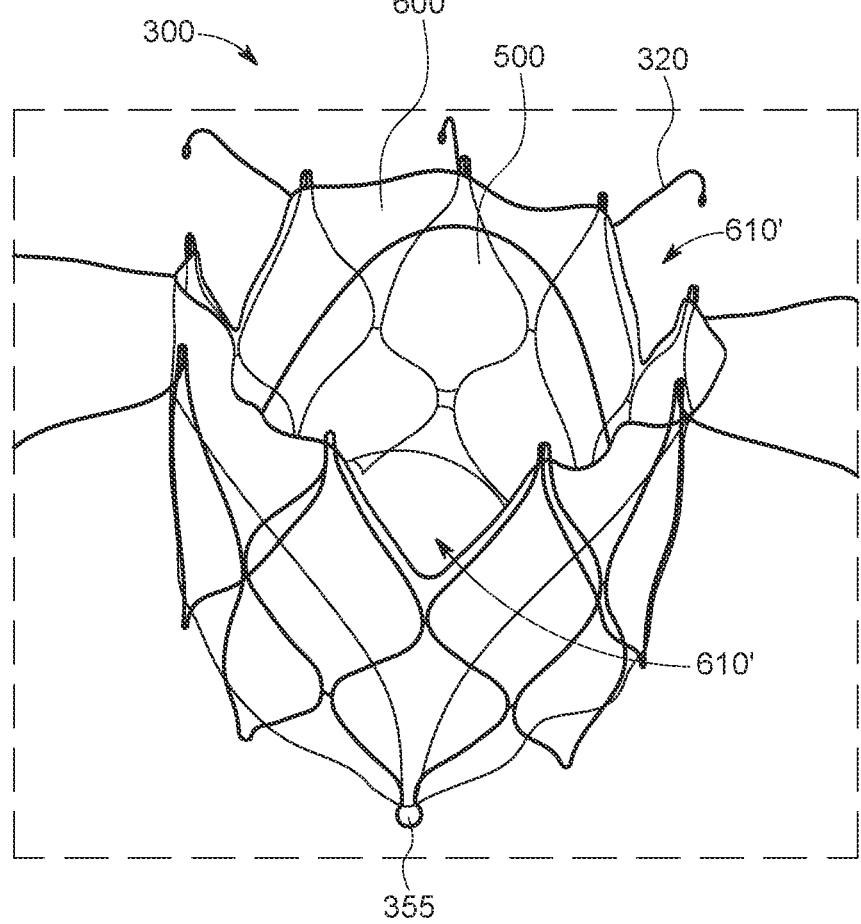
FIG. 4 is a perspective view of the inner frame of FIG. 2 with an alternate valve assembly mounted to the inner frame.

An exemplary inner frame 300 and valve assembly are described below before returning to the description of the assembled prosthetic heart valve 10. FIG. 2 illustrates an exemplary inner frame 300 that may be used with prosthetic heart valve 10, with the inner frame 300 in an expanded or deployed configuration. FIG. 3 illustrates a similar inner frame 300 in an expanded or deployed condition, with a valve assembly coupled thereto, the valve assembly including a plurality of prosthetic leaflets 500 and a sealing skirt 600. Referring to FIGS. 3 and 4, the inner frame 300 may be formed from a shape-memory material, such as Nitinol, and in some embodiments may be cut (e.g., laser cut) from a single tube. In the illustrated embodiment, the inner frame 300 is substantially cylindrical in the expanded or deployed condition, which may assist with optimal coaptation of the prosthetic leaflets 500 mounted to the inner frame 300. In the illustrated embodiment, the inner frame 300 includes an inflow row of cells 311*a*, and an outflow row of cells 311*b*, which may be generally diamond-shaped, although other shapes of cells (and other numbers of cells or numbers of rows of cells) than are shown may be suitable. A plurality of commissure attachment features ("CAFs") 355 may be provided on the inner frame 300 (e.g., integrally formed with the inner frame 300 or separately coupled). The number of CAFs 355 may be the same as the number of prosthetic leaflets 500 provided with prosthetic heart valve 10. For example, if three prosthetic leaflets 500 are provided, as shown in the embodiment of FIG. 3, three CAFs 355 may be provided on inner frame 300. The CAFs 355 may primarily function to serve as an attachment point of two adjacent prosthetic leaflets 500 to each other and/or to the inner frame 300. In the illustrated embodiment, each CAF 355 extends in the outflow direction from an outflow apex of a cell in the outflow row of cells 311*b*. Preferably, the CAFs 355 are positioned at substantially equal intervals around the perimeter of the inner frame 300. In the particular illustrated embodiment, each CAF 355 includes a two-by-two arrangement of generally circular or rectangular (e.g., square)

eyelets, with an elongated rectangular eyelet positioned on the inflow side of the two-by-two arrangement of eyelets. Some or all of these eyelets may be used to receive sutures or other fasteners that pass through one or both of the adjacent prosthetic leaflets 500 being coupled to the corresponding particular CAF 355. However, it should be understood that the configuration of CAFs 355 shown in FIG. 2 is merely illustrative, and other designs of CAFs (including the use of non-metal CAFs or using the cellular structure of the inner frame as CAFs) may be suitable for use with prosthetic heart valve 10.

Still referring to FIG. 2, the inner frame 300 may include a plurality of connecting arms 320 extending radially outwardly and in the outflow direction of the inner frame 300. Preferably, the connecting arms 320 may be formed integrally with the rest of the inner frame 300, but in other embodiments, they may be formed as separate components that are later coupled (e.g., via mechanical fasteners such as rivets or sutures, via adhesives, etc.) to the inner frame 300. Preferably, the connecting arms 320 are formed of a shape memory material such as Nitinol, but the connecting arms 320 may be formed of other materials, including other metals or metal alloys such as stainless steel. Referring to FIG. 2, each connecting arm 320 may have a first end connected to (including via being integrally formed with) a post 322 extending in the inflow direction from an inflow apex of each cell in the inflow row of cells 311*a*. Posts 322 may have shapes, sizes, and configurations different than those shown. For example, posts 322 may be shortened compared to those shown in FIG. 2, with a single hole instead of two holes as shown in FIG. 2. If posts 322 includes holes (e.g., two as shown, or a single hole as described above), the hole(s) may be used when sewing to the inner cuff (e.g., inner sealing skirt 600 described below) to prevent the fabric from sliding down the strut(s) of the inner frame 300. Although in the illustrated embodiment, inner frame 300 includes one connecting arm 320 coupled to each cell in the inflow row of cells 311*a*, it should be understood that fewer than all of the cells in the inflow row of cells 311*a* may include a connecting arm 320 extending therefrom. Each of the connecting arms 320 may extend to a second free end 324. In the illustrated embodiment, each second free end 324 includes an aperture defined therein which may be used to assist in coupling each connecting arm 320 to the outer frame 100. Although connecting arms 320 are shown in FIG. 2 are shown as extending mostly linearly at an acute angle toward the outflow end of the inner frame 300, it should be understood that other contours and shapes may be suitable. For example, a number of other options for the shape and/or contours of connecting arms 320 are shown and described in connection with U.S. Provisional Patent Application No. 63/304,830, filed Jan. 31, 2022, and titled "Flexible Heart Valve With Arm Attachment to Outside Structure," the disclosure of which is hereby incorporated by reference herein.

FIG. 3 shows the inner frame 300 of FIG. 2, with a sealing skirt 600 coupled to the luminal surface of frame 300 and a plurality of prosthetic leaflets 500 coupled to the skirt 600 and CAFs 355 to form a valve assembly. In FIG. 3, the connecting arms 320 are shown with a slightly different contour than shown in FIG. 2. For example, the connecting arms 320 are shown in FIG. 3 as extending at an angle that is closer to perpendicular to the central longitudinal axis of the inner frame 300. In other words, the arms 320 of inner frame 300 shown in FIG. 3 extend at an angle of between about 60 degrees and about 90 degrees with respect to the central longitudinal axis of the inner frame 300, including at an angle of about 70 degrees or about 80 degrees. Further, the connecting arms 320 shown in FIG. 3 have more of an "S"-shape contour in which the connecting arms 320 have a point of inflection near the middle of the arms 320 between the first end and the free end 324. Generally, the connecting arms 320 may help to isolate the valve assembly and the inner frame 300 carrying the valve assembly from forces exerted on the outer frame 100. As the native valve annulus changes shape during normal operation of the heart (e.g., cycling between systole and diastole), forces are applied to the outer frame 100 that is in contact with the native valve annulus, and those forces may deform the shape of the outer frame 100. Despite such deformation, the connecting arms 320 may help absorb or otherwise reduce or dampen forces on the outer frame 100 from transmitting to the inner frame 300 and causing the inner frame 300 (and thus the valve assembly) to significantly deviate from the desired cylindrical shape. It should be understood that, although connecting arms 320 are shown and described as being part of the inner frame 300 and connected to the outer frame 100, in some embodiments the connecting arms may instead be part of the outer frame 100 and connected to the inner frame 300, or separate components coupled to the inner and outer frames. Still further, in other embodiments the inner frame 300 may include a first group of connecting arms extending outwardly, and the outer frame 100 may include a second group of connecting arms extending inwardly, with the two groups of arms being connected to each other to couple the two frames together.

Referring to FIG. 3, a plurality of prosthetic leaflets 500 may be mounted within the inner frame 300 to provide the desired valve functionality. In the illustrated example, three prosthetic leaflets 500 are provided, although in other examples more or fewer than three prosthetic leaflets may be provided. In the particular example shown in FIG. 3, each prosthetic leaflet 500 includes a generally "U"-shaped or scalloped edge that is connected to the inner frame 300 and/or to the sealing skirt 600 along the connected edge. Each prosthetic leaflet 500 may also include a free edge opposite the connected edge, the free edges of the prosthetic leaflets 500 being configured to move toward and away from each other to close or open the valve assembly, respectively. Each prosthetic leaflet 500 may also include a pair of tabs where the free edge intersects with the connected edge, and tabs of adjacent prosthetic leaflets 500 may be coupled to each other and/or the inner frame 300 via the CAFs 355. However, the number and particular shape of the prosthetic leaflets 500 may be other than the specific example shown. In some embodiments, the prosthetic leaflets 500 are formed of tissue, for example, bovine or porcine pericardium. In other examples, the prosthetic leaflets 500 are formed of synthetic materials, such as polymer sheets or woven fabrics formed of PET, PTFE, etc.

Still referring to FIG. 3, the sealing fabric 600 may be positioned interior to the inner frame 300 (although in some embodiments it may be positioned exterior to, or on both surfaces of, the inner frame 300. The sealing fabric 600 need not be an actual fabric and may be a tissue such as bovine or porcine pericardium, a polymer sheet material, or a fabric such as a woven fabric of PET, PTFE, or other materials. In some embodiments, the sealing fabric 600 may have a generally tubular or cylindrical shape and extend along most or all of the inner surface of the inner frame 300. However, in some examples, the sealing fabric 600 may stop short of one or both terminal ends of the inner frame 300. The sealing fabric 600 may be connected to the inner frame 300 by any suitable mechanism, including for examples sutures that generally follow and couple to the struts that form the cells of the inflow row of cells 311a and the outflow row of cells 311b. In addition to helping to ensure that blood does not flow through the open cells of the inner frame 300, the sealing fabric 600 may also serve as the primary mode of connecting (e.g., via sutures) the prosthetic leaflets 500 to the inner frame 300, although as described above, the CAFs 355 may also serve to connect the prosthetic leaflets 500 to the inner frame 300.

Referring back to FIG. 1, the prosthetic heart valve 10 may be formed by coupling the inner frame 300 to the outer frame 100 via the connecting arms 320. For example, the free ends 324 of the connecting arms 320 may be coupled to the outer frame 100 by any suitable mechanism. In some embodiments, sutures may be used to couple the free ends 324 of the connecting arms 320 (e.g., through the apertures therein) to the frame structure of the outer frame 100, including to areas of the frame where two adjacent atrial cells 111a intersect. In some embodiments, certain struts of the outer frame 100 may include apertures that correspond to those in the free ends 324 of the connecting arms 320. For example, the points at which adjacent atrial cells 111a intersect may be provided with an aperture or hole therein, and each aperture in the free ends 324 of the connecting arms 320 may be aligned with a corresponding aperture in the outer frame 100, and the connecting arm 320 may be coupled to the outer frame 100 with the assistance of the complementary apertures (e.g., sutures or rivets or other mechanical fasteners passing through the complementary apertures). It should be understood that other features may be included on the connecting arms to assist with the coupling, including multiple apertures instead of one aperture, one or more slots, and/or complementary features on the inner or outer frame at the desired connection point, such as apertures, slots, etc.

As described above, prosthetic heart valve 10 may include a sealing skirt on the outer surface of the outer frame 100. In the illustrated embodiment, the sealing skirt has an outflow edge that is a spaced distance from the terminal outflow end of the ventricular cells 111b. With this configuration, the sealing skirt 200 may not extend so far into the ventricle as to cause significant obstruction of the left ventricular outflow tract ("LVOT") if the prosthetic heart valve 10 is implanted in the mitral valve, or the right ventricular outflow tract ("RVOT") if the prosthetic heart valve 10 is implanted in the tricuspid valve. However, in some embodiments, the sealing outflow edge of skirt 200 may extend farther to cover the terminal outflow end of the ventricular cells 111b. Similarly, the inflow edge of the sealing skirt 200 may stop short of the pins or tabs 122 so as to not interfere with suture loops or similar structures of a delivery device from engaging or disengaging with the pins or tabs 122.

Sealing skirt 200 may help seal against blood leaking around the outside of the outer frame 100 and leaking through open cells 111a-c of the outer frame 100. However, after inner frame 300 is coupled to outer frame 100, there is a gap between the inner frame 300 and outer frame 100 that may need to be covered or otherwise sealed so that blood does not leak through that space. As shown in FIG. 1, a bridging skirt 220 may extend radially inwardly from an inflow portion of the sealing skirt to the sealing skirt 600 on the inner frame 300. The outer perimeter of bridging skirt 220 may be sutured to or otherwise fastened to the sealing skirt 200, and the inner perimeter of the bridging skirt 220 may be sutured or otherwise fastened to the sealing skirt 600. With this configuration, the combination of skirts 200,

220, 600 helps to ensure that any blood flowing through or past the prosthetic heart valve 10 is required to flow through inner frame 300 and only when the prosthetic leaflets 500 are open. In some embodiments, the bridging skirt 220 may follow the contours of the connecting arms 320, and in some embodiments, the bridging skirt may be coupled (e.g., via sutures or other fasteners) to the connecting arms 320. Although the sealing skirt 200, bridging skirt 220, and sealing skirt 600 may be formed as separate members, in other embodiments, two or more of the skirts may be formed as an integral or single member.

One potential benefit of the configuration of the prosthetic heart valve 10 shown in FIG. 1 is that the inner frame 300 and correspondingly the valve assembly mounted to the inner frame 300 is "atrialized." In other words, the position of the inner frame 300 is shifted more toward the atrium than the ventricle. This positioning of the inner frame 300 may reduce the likelihood that the inner frame 300 and/or the valve assembly mounted to the inner frame has any interactions with the sub-valvular apparatus (e.g., chordae tendineae), which interaction could lead to patient injury and/or malfunction of the prosthetic valve 10.

Although there may be benefits if the inner frame 300 has the "atrialized" positioning shown in FIG. 1, or a similar positioning, there may also be certain drawbacks involved. For example, if the inner frame 300 protrudes into the atrium, the orifice through which blood flows when the prosthetic leaflets 500 are open is positioned "higher" than other structures on the inflow side of the native annulus. This relative positioning may risk turbulent flow or stagnation of blood against the "lower" portions of the prosthetic heart valve 10. Stagnation of blood may lead to a risk of blood clotting on the prosthetic heart valve 10 in the areas of stagnation, which may lead to a potential embolization and injury to the patient.

The potential problem of blood puddling or stagnation may be a greater risk with tricuspid valve replacements compared to mitral valve replacements. For example, transcatheter prosthetic heart valves that are implanted in the mitral valve may include skirts and/or cuffs that may form a generally continuous and smooth connection with the native anatomy, which may reduce the ability of blood to stagnate around the prosthesis. The tricuspid valve typically has a different anatomy than the mitral valve, with the tissue around the tricuspid valve being more planar with the tricuspid valve annulus compared to the shape of the mitral valve annulus. As a result, for prosthetic heart valves that otherwise have similar designs for replacing the mitral valve or the tricuspid valve, prosthetic tricuspid valves may typically require a shallower and flatter atrial portion of the outer frame 100, which may increase the risk of blood stagnating at the prosthesis. The significantly lower pressures that exist in the right heart may also create a higher risk of stagnation compared to the left heart which has higher pressures. Still further, for prosthetic heart valves that include connecting arms to connect an inner frame to an outer frame, certain arm designs may simply make it difficult to move the inner frame toward the ventricle, which may allow for a more natural "funnel" action of blood flowing toward the prosthetic heart valve while minimizing stagnation. And while connecting arms may be redesigned to lay flat, compared to the angle shown in FIG. 2 for example, to help to "ventricularize" the inner frame, other prosthesis design concerns (e.g., oversizing of the outer frame) and other anatomical situations (e.g., an irregularly shaped annulus), may still nonetheless result in the "atrialization" of the inner frame which may increase the risk of blood stagnation.

Figure 5:
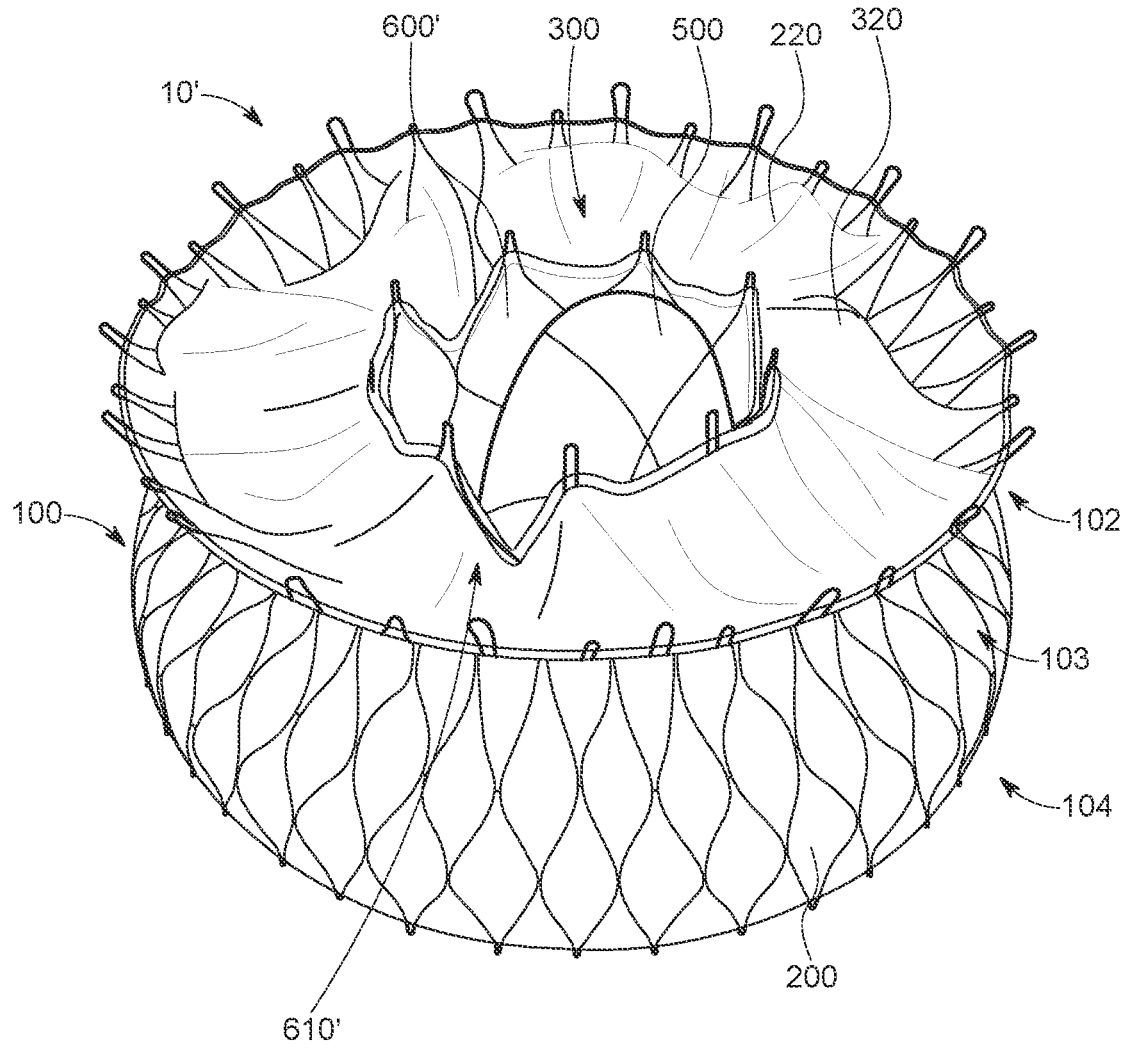
FIG. 5 is a perspective view of a prosthetic heart valve incorporating the inner frame and valve assembly of FIG. 4.

One option to maintain a relatively "atrialized" inner frame, similar or identical to inner frame 300, while minimizing the likelihood of blood stagnation, is to introduce features into the prosthetic heart valve to "guide" or "drain" blood so that it follows the desired path into and through the inner frame 300 without stagnating. One exemplary mechanism by which this may be achieved is shown in FIGS. 4-5, which illustrate a prosthetic heart valve 10' that is identical to prosthetic heart valve 10 with only one difference. Thus, only the differences are described below.

Referring to FIG. 4, inner frame 300 is shown that is identical to inner frame 300 of FIG. 3. Inner frame 300 may have a valve assembly mounted therein that includes a plurality of prosthetic leaflets 500 that may be identical to prosthetic leaflets 500 of FIG. 3. The valve assembly of FIG. 4 may include a sealing skirt 600' that is nearly identical to sealing skirt 600', with the only exception being one or more recesses, drains, or trenches 610' formed in the sealing skirt 600'. For example, as shown in FIG. 4, the inflow edge of the sealing skirt 600' may follow a generally circular pattern, but at the trenches 610', the inflow edge of the sealing skirt 600' may extend in a direction toward the outflow end. In the specific example shown, sealing skirt 600' includes three trenches 610', and each trench 610' is formed by the inflow edge of the sealing skirt 600' following along two struts of adjacent cells in the atrial row of cells 311a to form a generally "V"-shaped recess or opening. In other embodiments, a different number and/or different shape of trenches 610' may be provided, and the trenches 610' may be provided at equal or unequal intervals around the perimeter of the inflow edge of the sealing skirt 600'. Further, in the illustrated embodiment, each trench 610' is axially aligned with one of the CAFs 355, although this positioning is not necessary. It may be preferable to have this alignment, however, because this alignment may allow the trench 610' to be relatively deep since the prosthetic leaflets 500 have their greatest spacing from the inflow end of the inner frame 300 at the CAFs 355.

Referring now to FIG. 5, a prosthetic heart valve 10' is shown that is identical to prosthetic heart valve 10, with the exception being that the inner frame 300 with sealing skirt 600' is coupled to the outer frame 100, instead of the inner frame 300 with sealing skirt 600. The bridging skirt 220 illustrated in FIG. 5 may be the same as the bridging skirt 220 illustrated in FIG. 1, and may again include an outer perimeter that is coupled to the sealing skirt 200 and an inner perimeter that is coupled to the inflow edge of the sealing skirt 600'. In some embodiments, the bridging skirt 220 shown in FIG. 5 may be slightly altered compared to the bridging skirt 220 shown in FIG. 1, for example having a different cut pattern where the bridging skirt 220 couples adjacent to the trenches 610', as described in greater detail below. However, because of the existence of the trenches 610', the bridging skirt 220 may form a channel or a preferential flow path that leads along the bridging skirt 220 into the trenches 610', which may allow for blood that would otherwise stagnate on the surfaces of the bridging skirt 220 to "drain" into through the trenches 610', at which point the blood may continue flowing through the opening defined by the prosthetic leaflets 500 and into circulation. For example, the lowest (or most "outflow") points on the bridging fabric 220 may be connected to the bottom of the trenches 610' or drains, allowing blood that might otherwise stagnate on the bridging skirt 220 to flow "downhill" or drain without stagnating, clotting, or embolizing. Stated differently, the trench may be sloped to empty residual fluid toward an outflow direction of the prosthetic heart valve. It should be understood that, although the prosthetic heart valve 10' may be particularly well suited for use as a prosthetic tricuspid valve to mitigate the potentially higher likelihood of blood stagnation, prosthetic heart valve 10' may still be well-suited for use in mitral valve replacements.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A prosthetic heart valve for replacing a native heart valve, the prosthetic heart valve comprising:

a collapsible and expandable outer frame configured to be positioned within an annulus of the native heart valve, an outer sealing skirt being positioned on a luminal or abluminal surface of the outer frame;

a collapsible and expandable inner frame;

an inner sealing skirt positioned on a luminal or abluminal surface of the inner frame;

a plurality of prosthetic leaflets coupled to the inner sealing skirt or the inner frame, and positioned within the inner frame;

a plurality of connecting arms connecting the inner frame to the outer frame so that the inner frame is positioned radially inward of the outer frame; and a bridging skirt extending from the outer sealing skirt to an inflow edge of the inner sealing skirt, the bridging skirt covering a gap between the inner frame and the outer frame, wherein the inner sealing skirt includes at least one trench that interrupts an otherwise circular shape of the inflow edge of the inner sealing skirt, the trench being sloped to empty residual fluid toward an outflow direction of the prosthetic heart valve.

2. The prosthetic heart valve of claim 1, wherein the inner frame includes cells arranged circumferentially in an atrial row of cells.

3. The prosthetic heart valve of claim 2, wherein the at least one trench forms a "V"-shape that follows struts of two circumferentially adjacent cells in the atrial row of cells.

4. The prosthetic heart valve of claim 3, wherein the at least one trench includes a plurality of trenches.

5. The prosthetic heart valve of claim 4, wherein the plurality of trenches includes three trenches.

6. The prosthetic heart valve of claim 5, wherein the inner frame includes three commissure attachment features extending at an outflow end of the inner frame, adjacent ones of the plurality of prosthetic leaflets being coupled to a corresponding one of the commissure attachment features, each of the three trenches being axially aligned with a corresponding one of the three commissure attachment features.

7. The prosthetic heart valve of claim 4, wherein, the inflow edge of the inner sealing skirt traverses a circumferential arc along an inflow end of the inner frame in a circumferential direction of the inner frame between circumferentially adjacent pairs of the plurality of trenches, so that the "V"-shapes of the plurality of trenches are positioned in the outflow direction of the prosthetic heart valve compared to the arc.

8. The prosthetic heart valve of claim 7, wherein the bridging skirt includes an outer perimeter attached to the outer sealing skirt, and an inner perimeter attached to the inner sealing skirt.

9. The prosthetic heart valve of claim 8, wherein the inner perimeter of the bridging skirt follows the circumferential arc of the inflow edge of the inner sealing skirt between adjacent pairs of the plurality of trenches, and follows the "V"-shapes of the plurality of trenches at the trenches.

10. The prosthetic heart valve of claim 9, wherein in an expanded condition of the prosthetic heart valve, bottoms of the "V"-shapes of the plurality of trenches are positioned at outflow-most positions of the bridging skirt.

11. The prosthetic heart valve of claim 10, wherein in an implanted condition of the prosthetic heart valve, the bridging skirt in combination with the inner sealing skirt form flow pathways that preferentially channel blood that flows toward the bridging skirt to drain into the inner frame via the plurality of trenches.

12. The prosthetic heart valve of claim 1, wherein the plurality of connecting arms have a first end coupled to the inner frame, and a second free end opposite the first end, the second free ends of the plurality of connecting arms being coupled to the outer frame.

13. The prosthetic heart valve of claim 12, wherein the second free ends of the plurality of connecting arms each define an aperture, the second free ends of the plurality of connecting arms being coupled to the outer frame via fasteners passing through the apertures.

14. The prosthetic heart valve of claim 13, wherein the fasteners are sutures or rivets.

15. The prosthetic heart valve of claim 12, wherein the first end of each of the plurality of connecting arms is formed integrally with the inner frame.

16. The prosthetic heart valve of claim 12, wherein in an expanded condition of the prosthetic heart valve, the plurality of connecting arms maintain an inflow end of the inner frame at an axial distance from an inflow end of the outer frame, so that the inflow end of the outer frame is positioned in an outflow direction of the prosthetic heart valve relative to the inflow end of the inner frame.

17. The prosthetic heart valve of claim 1, wherein the outer sealing skirt is a separate structure from the bridging skirt, and the bridging skirt is a separate structure from the inner sealing skirt.

18. The prosthetic heart valve of claim 17, wherein an outer perimeter of the bridging skirt is sutured to the outer sealing skirt, and an inner perimeter of the bridging skirt is sutured to the inner sealing skirt.

19. The prosthetic heart valve of claim 18, wherein the bridging skirt is sutured to the plurality of connecting arms.

20. The prosthetic heart valve of claim 1, wherein the prosthetic heart valve is sized and shaped for replacing a native right atrioventricular valve.

* * * * *